US006733777B2

(12) United States Patent
Erbacher et al.

(10) Patent No.: US 6,733,777 B2
(45) Date of Patent: May 11, 2004

(54) CATIONIC REAGENTS OF TRANSFECTION

(75) Inventors: Christoph Erbacher, Haan (DE); Martin Weber, Leichlingen (DE)

(73) Assignee: Qiagen GmbH, Hilden (DE)

(*) Notice: Subject to any disclaimer, the term of this patent is extended or adjusted under 35 U.S.C. 154(b) by 0 days.

(21) Appl. No.: 09/304,995

(22) Filed: May 4, 1999

(65) Prior Publication Data

US 2001/0048939 A1 Dec. 6, 2001

Related U.S. Application Data

(63) Continuation of application No. PCT/EP97/06035, filed on Nov. 3, 1997.
(60) Provisional application No. 60/030,315, filed on Nov. 4, 1996.

(51) Int. Cl.$^7$ .............................................. H61K 9/127
(52) U.S. Cl. ...................... 424/450; 514/44; 435/320.1; 435/455; 435/458
(58) Field of Search .............................. 424/70.78, 450; 514/44; 435/455, 458

(56) References Cited

U.S. PATENT DOCUMENTS

| 5,733,572 A | * | 3/1998 | Unger et al. ................ 424/450 |
| 5,744,335 A | * | 4/1998 | Wolff et al. ............... 435/172.3 |
| 5,780,448 A | * | 7/1998 | Davis .......................... 514/44 |
| 6,121,482 A | * | 9/2000 | Kwetkat et al. ............. 560/169 |
| 6,180,784 B1 | * | 1/2001 | Wolff et al. ................. 540/474 |

FOREIGN PATENT DOCUMENTS

WO    WO 96/25388    * 8/1996

OTHER PUBLICATIONS

R.Zana et al., Micellization of Two Triquatenary Ammonium Surfactants in Aqueous Solution, Langmiur 1995, Vol 11, pp. 3694–3698.*

M. Frindi et al., Alkanediyl–x,w–bis(dimethylakylammonium bromide) Surfactants. 4. Ultrasonic Absorption Studies of Amphiphile Exchange between Miceles and Bulk Phase in Aqueous Micellar Solutions, Langmuir 1994, Vol 10, pp. 1140–1145.*
R.Zana et al., Alkanediyl–x,w–bis(dimethylaklylammonium bromide) Surfactants. 1. Effect of the Spacer Chain Length on the Critical Micelle Concentration and Micelle Ionization Degee, Langmiur 1991, Vol 7, pp. 1072–7075.*
Buchberger et al., Dosper Liposomal Transfection Reagent: A Reagent with Unique Transfection Properties, 1996, Biochemia, No. 2, pp. 7–10.*
Anderson, Nature, vol. 392, 25–30, Apr. 1998.*
Verma et al. (Nature, vol. 389, 18, pp. 239–242, Sep. 1997).*
Sato et al. (Science, vol. 273, 1996, pp. 352–354).*
Branda et al. (J. of Laboratory and Clinical Medicine, 128, 3, pp. 329–338 1996).*
Weiner et al. (PNAS, vol. 94, pp. 10833–10837, 1997).*
McCluskie et al. (Critical Reviews in Immunology, 19, 303–329, 1999).*
Raz et al. (Vaccines, 94, pp. 71–75, 1994).*
Filion et al. (International J. of Pharmaceutics, 162, pp. 159–170, 1998).*

* cited by examiner

*Primary Examiner*—Dave T. Nguyen
(74) *Attorney, Agent, or Firm*—Leon R. Yankwich; David G. O'Brien

(57) ABSTRACT

Cationic cytofectins and liposomes comprising the same are disclosed which are especially useful for delivering exogenous compounds into cells in vitro and in vivo. The liposomes may comprise (a) a neutral lipid such as dioleoylphosphatidyl-ethanolamine (DOPE) or similar lipid-like compounds such as 1,2-dioleoyl-oxiphosphatidylethanolamine or other lipid-like structures and (b) one or more of the cationic cytofectins provided herein. The invention provides transfection kits and methods for delivery of exogenous compounds into cells.

48 Claims, No Drawings

CATIONIC REAGENTS OF TRANSFECTION

CROSS-REFERENCE TO RELATED APPLICATIONS

The present application is a continuation of copending international application PCT/EP97/06035, filed Nov. 3, 1997 and designating the United States, which international application claims priority to U.S. provisional application No. 60/030,315, filed Nov. 4, 1996.

TECHNICAL FIELD OF THE INVENTION

The present invention relates to cationic reagents for transfection, useful for delivery of exogenous compounds into cells, in vitro and in vivo.

BACKGROUND OF THE INVENTION

Currently four main methods for introducing nucleic acids into eukaryotic cells are in use: (1) electroporation; (2) calcium-phosphate-based transfection; (3) DEAE-dextran-based transfection; and (4) liposome-mediated transfection.

Compared to other methods, liposome-mediated transfection is characterized by high reproducibility, low cytotoxicity and simple procedures. However, many cationic compounds useful for liposome-mediated transfection are based on ester-linkages and are rapidly degraded by hydrolysis. Compared to infectious agents, cationic liposomes often show low overall efficiencies. Moreover, the commercially available cationic liposomes cannot be used or adapted for transfection of specific subpopulations of cells either in vitro or in vivo.

Advantages of the Invention Over Existing Technologies

The compounds of the present invention are easily preparable from inexpensive reagents, and therefore highly suitable for the preparation of liposomes for large-scale use. The compounds of Formula (I) are not based on ester-linkages, therefore, they are not degraded by hydrolysis. Transfection using the compounds of the present invention results in a high overall transfection efficiency. Adaption for transfection of specific cells is easily possible by structural changes of the compounds of the present invention and by choice of the accompanying counter ion. The compounds of the present invention provide an easy and reproducible procedure for liposome preparation, preferably without the need for sonication.

SUMMARY OF THE INVENTION

The present invention relates to compounds of Formula (I) useful for delivery of exogenous compounds into cells, in vitro and in vivo.

The present invention further provides liposomes comprising (a) a neutral lipid such as dioleoylphosphatidylethanolamine (DOPE) or similar lipid like compounds such as 1,2-dioleoyloxiphosphatidylethanolamine or other lipid-like structures and (b) one or more of the compounds of Formula (I). The present invention also relates to methods of delivery of exogenous compounds, for example macromolecules and pharmaceutical compositions, into cells in vitro and in vivo using the compounds of the present invention.

Also within the scope of this invention are transfection kits comprising the compounds of the present invention.

According to the present invention, the delivery of desired exogenous compounds to target cells may be modulated by, among other things, varying the following: (1) the structure of the compounds of Formula (I), (2) the ratio of neutral lipids to the compounds of Formula (I), (3) the method of preparing liposomes, or (4) the counter ion being prepared with the compounds of the present invention.

DETAILED DESCRIPTION

The present invention provides compounds of Formula (I):

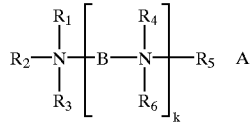

wherein

A denotes an anion selected from the group of chloride, bromide, iodide, hydrogenphosphate ($HPO_4^{2-}$), dihydrogenphosphate ($H_2PO_4^-$), sulphate, thiosulphate, hydroxy and/or oxalate.

k denotes an integer 1, 2, 3, 4 or 5;

B denotes an alkandiyl bridge $(CH_2)_n$ wherein n denotes an integer 1, 2, 3, 4, 5, 6, 7, 8, 9 or 10;

$R_1$, $R_3$ and $R_4$, which may be identical to one another or different, denote hydrogen, straight-chained or branched $C_1$–$C_6$-alkyl, $C_1$–$C_6$-alkenyl, $C_1$–$C_6$-alkynyl;

$R_2$ denotes straight-chained or branched $C_8$–$C_{20}$-alkyl, $C_8$–$C_{20}$-alkenyl, $C_8$–$C_{20}$-alkynyl;

$R_5$ denotes for k=1 straight-chained or branched $C_8$–$C_{20}$-alkyl, $C_8$–$C_{20}$-alkenyl, $C_8$–$C_{20}$-alkynyl;

denotes for k>1 hydrogen, straight-chained or branched $C_1$–$C_6$-alkyl, $C_1$–$C_6$-alkenyl, $C_1$–$C_6$-alkynyl;

$R_6$ denotes for k=1 hydrogen, straight-chained or branched $C_1$–$C_6$-alkyl, $C_1$–$C_6$-alkenyl, $C_1$–$C_6$-alkynyl;

denotes for k>1 a straight-chained or branched $C_8$–$C_{20}$-alkyl, $C_8$–$C_{20}$-alkenyl, $C_8$–$C_{20}$-alkynyl and the repeating unit —B—$NR_4R_6$ may be identical to one another or different.

Preferred are compounds of general Formula (I) wherein

A denotes an anion selected from the group of chloride, bromide, iodide, hydrogenphosphate($HPO_4^{2-}$), dihydrogenphosphate ($H_2PO_4^-$), sulphate, thiosulphate, hydroxy and/or oxalate.

k denotes an integer 1, 2 or 3;

B denotes an alkandiyl bridge $(—CH_2)_n—$ and n denotes an integer 1, 2, 3, 4, 5 or 6;

$R_1$, $R_3$ and $R_4$, which may be identical to one another or different, denote hydrogen or straight-chained or branched $C_1$–$C_6$-alkyl;

$R_2$ denotes straight-chained or branched $C_8$–$C_{20}$-alkyl, $C_8$–$C_{20}$-alkenyl, $C_8$–$C_{20}$-alkynyl;

$R_5$ denotes for k=1 a straight-chained or branched $C_8$–$C_{20}$-alkyl, $C_8$–$C_{20}$-alkenyl, $C_8$–$C_{20}$-alkynyl;

denotes for k>1 hydrogen, straight-chained or branched $C_1$–$C_6$-alkyl;

$R_6$ denotes for k=1 hydrogen, straight-chained or branched $C_1$–$C_6$-alkyl, $C_1$–$C_6$-alkenyl, $C_1$–$C_6$-alkynyl;

denotes for k>1 a straight-chained or branched $C_8$–$C_{20}$-alkyl, $C_8$–$C_{20}$-alkenyl, $C_8$–$C_{20}$-alkynyl and the repeating unit —B—$NR_4R_6$ is preferably identical to one another.

Specifically preferred are compounds of general Formula (I) wherein

A denotes an anion selected from the group of bromide, iodide, dihydrogenphosphate ($H_2PO_4^-$) and/or thiosulphate;

k denotes an integer 1 or 2;

B denotes for k=1
an alkandiyl bridge —$(CH_2)_n$— wherein
n represents an integer 2, 3 or 4;

B denotes for k=2
an ethylenebridge —$(CH_2$—$CH_2)$—;

$R_1$, $R_3$ and $R_4$ which are identical to one another denote $CH_3$;

$R_2$ denotes straight-chained $C_{10}$–$C_{20}$-alkyl;

$R_5$ denotes for k=1
straight-chained $C_{10}$–$C_{20}$-alkyl and is identical to $R_2$;
denotes for k=2
$CH_3$;

$R_6$ denotes for k=1
$CH_3$
denotes for k=2
straight-chained $C_{10}$–$C_{20}$-alkyl and is identical to $R_2$.

A pharmaceutically acceptable ion is a mono-, di- or multi-valent, preferably non cytotoxic, ion. The different salts can be synthesized by methods which are known per se from the state of the art, in particular using ion exchange methods.

$C_1$–$C_6$-alkyl generally represents a straight-chained or branched hydrocarbon radical having 1 to 6 carbon atoms which may optionally be substituted by one or several halogen atoms—preferably fluorine—which may be identical to one another or different. The following radicals may be mentioned by way of example:

methyl, ethyl, propyl, 1-methylethyl (isopropyl), butyl, 1-methylpropyl, 2-methylpropyl, 1,1-dimethylethyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2methyl-propyl.

The same definition applies accordingly to alkandiyl radicals.

$C_8$–$C_{20}$-alkyl refers specifically to a straight-chained or branched hydrocarbon radical having 8 or 20 carbon atoms—for example octyl, decyl, undecyl, dodecyl, tridecyl, tetradecyl, pentadecyl, hexadecyl, heptadecyl, dodecadecyl, nonadecyl and eicosyl.

Unless otherwise stated aklyl groups having 1 to 3 carbon atoms such as methyl, ethyl, n-propyl or isopropyl are preferred. The same definition applies to alkandiyl radicals.

Alkenyl in general represents a straight-chained or branched hydrocarbon radical having 3 to 6 carbon atoms and one or more double bonds, preferably one double bond, which may optionally be substituted by one or several halogen atoms—preferably fluorine—which may be identical to another or different. $C_8$–$C_{20}$-alkenyl refers specifically to a straight-chained or branched hydrocarbon radical having 8 or 20 carbon atoms and one or more double bonds.

Examples include:

2-propenyl (allyl), 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 3-methyl-4-pentenyl, 4-methyl-4-pentenyl, 1,1-dimethyl-2-butenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl.

The allyl group is preferred.

Alkynyl in general represents a straight chained or branched hydrocarbon radical having 3 to 6 carbon atoms and one or more triple or double bonds. $C_8$–$C_{20}$-alkynyl refers specifically to a straight-chained or branched hydrocarbon radical having 8 or 20 carbon atoms and one or more double or triple bonds.

Examples include:

2-propynyl (propargyl), 2-butynyl, 3-butynyl, 2-pentynyl, 3-pentynyl, 4-pentynyl, 3-methyl-2-butynyl, 2-hexynyl, 3-hexynyl, 4-hexynyl, 5-hexynyl, 3-methyl-2-pentynyl, 4-methyl-2-pentynyl, 2-methyl-3-pentynyl, 4-methyl-3-pentynyl, 1-methyl-4-pentynyl, 1,1-dimethyl-2-butynyl, 1,1-dimethyl-2-butynyl, 1,1-dimethyl-3-butynyl, 1,2-dimethyl-3-butynyl, 1,3-dimethyl-2-butynyl, 2,2-dimethyl-3-butynyl, 1-ethyl-2-butynyl, 1-ethyl-3-butynyl, 2-ethyl-3-butynyl, and 1-ethyl-1-methyl-2-propynyl.

A lower alkynyl radical (propargyl) having 3 carbon atoms and a triple bond which may optionally be substituted by one or several halogen atoms—preferably fluorine—which may be identical to another or different is preferred.

Liposomes useful in the delivery of exogenous compounds to cells are objects of this invention. In the context of the present invention, the term "liposome" denotes any structure comprising: (a) a neutral lipid or lipid like molecule and (b) one or more of the compounds of Formula (I). Said structures include double layers, aggregates, micelles and the like. A neutral lipid or lipid like molecule useful in preparing liposomes of this invention may be dioleoylphosphatidyl-ethanolamine (DOPE) and/or 1,2-dioleoyloxiphosphati-dylethanolamine and/or Cholesterole and/or Dioleylphosphatidylcholin (DOPC).

In one embodiment of this invention, two or more compounds of Formula (I), preferably with different cell specificity, may be combined with helper lipids or lipid similar structures for liposome preparations.

In another embodiment of this invention, lipid like molecules in which the ester linkage is replaced by a hydrolytically more stable linkage for a high hydrolytic stability may be prepared and used as helper lipids for liposome preparations.

In another embodiment of this invention, asymmetric hydrophobic side chains are contemplated.

In a preferred embodiment of this invention, the neutral lipid is DOPE. A co-lipid according to the present invention is a compound capable, alone or in combination, with other lipid components, to form a stable liposome, including but not limited to co-lipids selected from the following group: phospholipid-like compounds, such as lecithine, phosphatidylcholine, dioleyl-phosphatidylcholine (DOPC), phosphatidylethanolamine (PE), phosphatidylserine, phosphatidylglycerine, phosphatidylinositole, sphingomyeline, cephaline, cardiolipine, phosphatidic acid, cereoroside, diacetylphosphate, lysophosphatidylethanolamine, dipalmitoylphosphatidylcholine, dioleoylphosphatidylglycerol, dipalmitoylphosphatidylglycerol, palmitoyloleoylphosphatidylcholine, palmitoyloleoylphosphatidylethanolamine, diheptadecanoylphosphatidylethanolamine, dilauroylphosphatidylethanolamine, dimyristoylphosphatidylethanolamine, distearoylphosphatidylethanolamine, beta-linoleoyl-gamma-palmitoylphosphatidylethanolamine and beta-oleoyl-gamma-palmitoylphosphatidylethanolamine and the like, lipids not containing phosphorous, including but not limited to steroids, terpenes, stearylamine, dodecylamine, hexadecylamine, acetylpalmitate, glycerinericine-oleate, hexadecylstearate, isopropylmyristate, dioctadecyl-ammoniumbromide, amphoteric polymers, such as triethanoleamine-laurylsulfate, lysolecithin, and similar compounds.

In the context of the present invention, the term "compounds of the present invention" denotes compounds of Formula (I) or the above disclosed liposomes comprising the compounds of Formula (I).

In one embodiment, the compounds of the present invention comprise a cellular or sub-cellular targeting system for achieving desirable intracellular delivery of specific exogenous compounds, in the following denoted "transfection". The intracellular delivery can be into the cytoplasm and/or the nucleus and/or other organelles.

The term "transfection" in the context of the present invention more specifically denotes the introduction of an exogenous compound, for example macromolecules, preferably biologically active compounds, into a target cell, in vivo or in vitro. Preferably, chemical compounds, proteins or peptides which bind cell surface or subcellular compartments may be included in liposomes of this invention. In one embodiment, a cell targeting component in a liposome may be a ligand or ligand-like component for a specific cell surface receptor or nuclear receptor. Preferably, a ligand such as a hormone, a carbohydrate ligand, a growth factor, a neurotransmitter, or fragment thereof or a nuclear localization signal may be included to facilitate cellular or subcellular recognition by the liposome. In another embodiment, the cellular or subcellular targeting components are modified. Preferably, the cellular or subcellular targeting component may be covalently linked to the macromolecules described below.

Further selectivity can be achieved by incorporating specific molecules such as antibodies, lectins, peptides or proteins, carbohydrates, glycoproteins, and the like, on the surface of the liposome vesicles, which can then serve to "target" the drugs formulated with the compounds of the present invention to desired tissues bearing appropriate receptors or binding sites for the ligand attached to the vesicle surface. Further selectivity can also be achieved by coating the liposome vesicles with a neutral or negatively-charged optional co-lipid (to eliminate non-specific adsorption to cells) before addition of the targeting ligand as described above.

In another embodiment, the exogenous compound according to the present invention is a natural or synthetic nucleic acid, or a derivative thereof—single-stranded or double-stranded—, preferably genomic DNA, cDNA, plasmid DNA, DNA vectors (suitable vectors are disclosed for example in EP773295, published 14.05.97, which is fully incorporated by reference herein), oligonucleotides, or nucleosides, or RNA, for example mRNA (sense or antisense) or ribozymes, or DNA/RNA-hybrids. It should be appreciated that such DNA oligonucleotides may be complementary to the coding region, the 3' untranslated region, or a transcription control sequence of a gene. In one embodiment of the invention, the DNA oligonucleotides are modified to increase or decrease biodegradability of the oligonucleotide. In one embodiment, phosphodiester linkages between nucleotides may be replaced with alternative linkages such as phosphorothioate linkages or phosphoroamidate linkages.

Thus, formulations comprising: (1) compounds of the present invention, and (2) DNA or complementary DNA (cDNA)—in appropriate plasmids containing promoters, enhancers and the like undesired—, can be utilized to achieve transfection of cells and to obtain stable transfectants as part of the process of cloning (via recombinant DNA technology well known to those familiar in the art) various desired sequences to yield the corresponding expressed products (e.g., proteins and peptides).

The technology of utilizing a compound of the present invention to achieve efficient transfection and to obtain stable transfectants with the desired DNA sequences can significantly enhance the ability to achieve the desired end result of the cloning procedure.

This technology provides a less toxic and more efficient route for the delivery of poly-nucleotides to cells than other presently used techniques such as calcium phosphate precipitation.

In another embodiment of the present invention, the exogenous compound can be a natural or synthetic peptide or protein, or derivative thereof. Preferably, the peptide or protein, or derivative thereof, has antigenic properties. Derivatives of peptides or proteins are for example cyclic peptides or peptidomimetics, comprising non natural amino acids and/or non-natural bonds between the individual amino-acids. Other exogenous compounds according to the present invention are physiologically active compounds, for example hormones, i.e. steroids, and the like, carbohydrates, or pharmaceutical compounds.

Of particular interest is the use of the compounds of the present invention in pharmaceutical formulations, particularly topical formulations such as ointments, gels, pastes, creams, and the like; and more particularly for the preparation of pharmaceutical formulations containing liposomes. The consistency of the formulation depends on the amount of aqueous solution used to make the formulation. In such formulations containing compounds of this invention, drugs which are insoluble or only sparingly soluble themselves in aqueous solutions can be: solubilized so that a greater concentration of drug can be presented to the body.

In pharmaceutical formulations, the compounds of the present invention may be used in those contexts where cationic lipids are acceptable for the formulation of creams, pastes, gels, colloidal dispersions, and the like. For additional information, reference is made to Remington's Pharmaceutical Society, 17th Edition, Mark Publishing Company, Easton, Pa. (1985), or any other standard treatise on pharmaceutical formulations.

In another embodiment, the compounds of the present invention are useful in delivering biologically active molecules for therapeutic and/or prophylactic use, preferably as a prophylactic and/or therapeutic vaccine. In a preferred embodiment, the compounds of the present invention are useful in gene therapy and antisense therapy, preferably in the prophylaxis and/or therapy of humans, or non human animals. The compounds of the present can be used for the preparation of pharmaceutical compounds. The compounds of the present invention can be used for treatment of humans and non human animals.

In one embodiment of the present invention, the oligonucleotides comprise unmethylated CpG dinucleotides, which have been shown to activate the immune system (A. Krieg, et al., "CpG motifs in Bacterial DNA Trigger Directed B Cell Activation" Nature 374: 546–549 (1995)). Depending on the flanking sequences, certain CpG motifs may be more immuostimulatory for B cell or T cell responses, and preferentially stimulate certain species. Copies of CpG motifs in DNA expression vectors act as adjuvants facilitating the induction of an immune response against an expressed protein. A CpG motif, a stretch of DNA containing CpG dinucleotides within a specified sequence, may be as short as 5–40 base pairs in length. Multiple CpG motifs may be inserted into the non-coding region of the expression vector. When a humoral response is desired, preferred CpG motifs will be those that preferentially stimulate a B cell response. When cell-mediated immunity is desired, preferred CpG motifs will be those that stimulate secretion of cytokines known to facilitate a CD8+ T cell response.

In another embodiment, the CpG motifs are inserted into a plasmid DNA vector, said vector is then replicated in a bacterial cell, allowing the CpG motifs to retain their unmethylated form. Said vector, or parts thereof, is then harvested and delivered to a target cell by the liposomes of the present invention, as an immunostimulatory substance, or together with a vaccine, as an adjuvant.

Intracellular delivery using the compounds of the present invention can also be achieved in the whole organism and may be useful in several diverse applications. Preferably, enzyme-replacement therapy can be effected by direct intracellular introduction of the desired enzymes, or by appropriate transfection of cells with a DNA sequence encoding the desired protein, with the appropriate promoters and the like include so as to give sufficient gene expression. If desired, inducible promoters can be employed to allow control in turning on or turning of the gene of interest. Other applications of intracellular delivery that can be achieved employing the compounds of the present for transfection of DNA include but are not limited to hormone replacement therapy (e.g., insulin, growth hormone, etc.), blood coagulation factor replacement therapy, replacement therapy for other blood disorders such as, β-thalassemia or other hemoglobin deficiencies, adenosine deaminase deficiency, neurotransmitter replacement therapy, and the like. Another application utilizing such formulations to enhance intracellular delivery includes the delivery of "antisense" RNA oligomers to collectively turn off expression of certain proteins. The compounds of the present invention can also be used to deliver biologically active materials across the blood brain barrier.

Preferred DNA/liposome ratios for use in in vivo delivery systems comprise DNA/liposome ratios in the range of (w/w) 2:1 to 1:3, 1 μg to 100 mg per kg body weight, i.e. for:

Cystic Fibrosis:
Mouse: DNA/lipid (w/w) 2:1, 5 mg to 100 mg, i.e. 10 mg to 80 mg, DNA per kg body weight;
Human: DNA/lipid (w/w) 1:5, 100 μg to 8 mg, i.e. 125 μg to 7.5 mg, DNA per kg body weight;

Coronary artery diseases:
Porcine: DNA/lipid (w/w) 1:3, 1 μg to 10 μg, i.e. 2 μg to 8 μg, DNA per kg body weight In one embodiment of the present invention, the transfected cells (target cells) are preferably eukaryotic, cells or cell lines, more preferably animal cells, preferably fish cells, i.e. teleostei, i.e. salmon, trout, eel and the like; rodent cells, i.e. rat, mouse, hamster and the like; artiodactyl cells, i.e. porcine, bovine and the like; perissodactyl cells, i.e. equine and the like; simian cells, i.e. human, African green monkey and the like. Preferred cell types are epithelial cells, i.e. skin, lung, artery and the like; muscle cells and the like, nerve cells and the like; and germ line cells.

Preferred liposomes for in vivo application, preferably for the vaccination of fish, comprise the compounds of Formula (I) and DOPE. Highly preferred are Q203, Q205, Q206, Q208, and Q817 (see Table 1).

The compounds of the present invention may first be tested in transfection with DNA plasmids in cell lines and primary cells to determine their transfectability, followed by transfections in animals.

One embodiment of this invention includes the systemic, topical or localized administration of exogenous compounds with the compounds of the present invention. Modes of systemic administration may include intramuscular, intravenous, intraperitoneal, or subcutaneous administration. Preferably, compounds of the present invention may be injected into patients. Another embodiment of this invention includes the administration of the compounds of the present invention by oral means, by transdermal means or by oral inhalation or intranasal inhalation.

Liposomes comprising exogenous compounds, for example biologically active substances, may be formulated into compositions suitable for administration. For example, for oral administration, a compound of the present invention may be given in the form of a capsule, tablet, or gel. In other embodiment, a compound of the present invention may be given in the form of an ointment, salves, gel, cream, patch, or suppository. The compounds of Formula (I) are particularly useful in the preparation of liposomes, but may be used in any of the many uses for which cationic lipids find application. For example, they may be used in industrial applications, in food or feeds, in pharmaceutical formulations, cosmetic compositions, or other areas where lipids may be employed.

The compounds of the present invention may also be used in cosmetics, for example, in makeups, lipstick, eyeshadow material, fingernail polishes, body lotions, moisturizing creams, and the like. They may also be used for application to the hair, either alone or in combination with other materials, such as in shampoos, hair conditioners, permanent wave formulations or hair straighteners, or as components in hair creams, gels, and the like.

In one embodiment of this invention, the compounds of the present invention are useful in delivering exogenous compounds, for example macromolecules, in vitro for laboratory use. Formulations comprising the compounds of the present invention can be used to transfect and transform cells in vitro to introduce a desired trait before implantation of the transformed cells into the whole organism. An example of this application is to transfect bone marrow cells with a desired gene, such as one coding for normal adult hemoglobin sequences to correct the deficiency in patients with disorders such as β-thalassemia, adenosine deaminase deficiency, and sickle-cell anemia The bone marrow cells can be transfected in vitro, and then the appropriately transfected cells can be transfused into the marrow of the patient. Alternatively, the cells can be transfected in vivo as described herein. Procedures such as calcium phosphate precipitation are much less efficient in effecting such transfections, making unsuitable for practical use. Other means of achieving transfection that have been applied in vitro include the use of viral vectors (such as SV-40 and retroviruses). However, these viruses are oncogenic and thus cannot be safely used for transfecting cells in vivo or in vitro formulate transfusion for in vivo intracellular delivery utilizing formulations of compounds of the present invention is also useful for delivery of antiviral compounds (such as protease inhibitors, nucleoside derivatives, nucleotides, or poly-nucleotides); and cancer compounds (including but not limited to nucleosides/nucleotides such as 5-fluorouracil, adenosine analogs, cytosine analogs, and purine analogs), antibiotics such as anthracylines (for example adriamycin and daunomycin) and bleomycin; protein antibiotics such as nuocarzinostatin, marcomomycin, and auromomycin; alkylating agents such as chlorambucil, cyclophosphamide, nitrosoureas, melphalan, aziridines, alkyl alkanesulfonates; platinum coorindation compounds; folate analogs such as methotrexate; radiation sensitizers; alkaloids such as vincristine and vinblastine; cytoskeleton-disrupting agents; differentiating agents; and other anti cancer agents. This aspect of the invention can be particularly useful in overcoming drug resistance such as caused by reduced uptake mechanisms of the drug by the cells.

Preferred DNA/liposome ratios for in vitro transfection of cell cultures are 0.01 μg to 10 μg DNA/μg liposome. Highly preferred are 0.1 μg to 1 μg DNA/μg liposome.

In one embodiment the present invention provides kits for transfection, comprising the compounds of the present invention, preferably together with suitable buffers.

In order that this invention may be more fully understood, the following examples are set forth. These examples are for the purpose of illustration only and are not to be construed as limiting the scope of the invention in any way.

EXAMPLES

Example 1

Synthesis of Cationic Cytofectins

All the following reactions were performed in dry acetonitrile or ethanol under reflux for 40 hours to 43 hours with argon protection. The solid product was separated from the reaction mixture by filtration, then washed with cold diethylether and recrystallized in diethylether/methanol and other solvent mixtures. The purity of the bis(quartemary ammonium) surfactants was checked by TLC on octadecyl silica plates with a mobile phase chloroform/methanol/n-propanol/ethylester/0.25% KCl aq 25/13/25/25/9 (v/v/v/v/v). No starting materials were found in these products.

A. alkanediyl-α,ω-bis(dimethyl alkyl ammonium bromides)

Two methods have been employed for the preparation of alkanediyl-α,ω-bis(dimethyl alkyl ammonium bromides). Such compounds include those of the following structure:

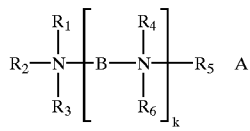

wherein
A=bromide (Br⁻), k=1; B denotes an alkandiyl bridge $(CH_2)_n$ wherein n=2, 3 or 4.

$R_1$, $R_3$, $R_4$, and $R_6$ denotes methyl —($CH_3$);
$R_2$ and $R_5$ denote even numbered straight-chained $C_8$–$C_{20}$-alkyl.

Method (a)

Reaction of α,ω-dibrom-propane or -butane with a 10% excess of N,N,N-decyldimethyl amine or N,N,N-dodecyldimethyl-amine or N,N,N-octadecyldimethyl-amine.

Method (b)

Reaction of alkanediyl-α,ω-bis(dimethyl amine) with a 10% excess of 1-bromo-n-octane, 1-bromo-n-decane, 1-bromo-n-dodecane, 1-bromo-n-tetradecane, 1-bromo-n-hexadecane and bromo-n-octadecane.

B. N,N',N"-trialkyl-N,N,N',N",N",-pentamethyl-bis-(2-ammonioethyl)ammoniumbromide Reaction of N,N,N',N",N"-pentamethydiethylenetriamine with a 5% excess of the appropriate 1-bromo-alkane to give N,N',N"-trialkyl-N,N',N",-pentamethyl-bis-(2-ammonioethyl)ammoniumbromide In this way, the following cationic cytofectins were prepared:

a) N,N',N"-trioctyl-N,N,N',N",N"-pentamethyl-bis-(2-arnmonioethyl)-ammoniumbromide
b) N,N',N"-tridecyl-N,N,N',N",N"-pentamethyl-bis-(2-ammonioethyl)-ammoniumbromide
c) N,N',N"-tridodecyl-N,N,N',N",N"-pentamethyl-bis-(2-ammonioethyl)-ammoniumbromide
d) N,N',N"-tritetradecyl-N,N,N',N",N"-pentamethyl-bis-(2-ammonioethyl) ammoniumbromide
e) N,N',N"-trihexadecyl-N,N,N',N",N"-pentamethyl-bis-(2-ammonioethyl)-ammoniumbromide
f) N,N',N"-trioctadcyl-N,N,N',N",N"-pentamethyl-bis-(2-ammonioethyl)-ammoniumbromide Example 2

Preparation of Cationic Cytofectins with Dihydrogenphosphate ($H_2PO_4$—) as Counter Ion Eight grams of dowex 1×8–400 anion exchange resin was extensively washed with 50% aqueous methanol in a chromatographic column. The column was further washed with twenty column volumes of 1M phosphoric acid, with distilled water until neutrality, and finally with ten column volumes of 50% methanol.

After these washing steps, a solution of cationic cytofectin in bromide form was dissolved in 50% methanol and then applied to the column. Next, 50% methanol was pumped through the column and twenty column volumes of the effluent were collected. The pH of the effluent was adjusted with phosphoric acid in order to prepare dihydrogenphosphates or hydrogenphosphates. The solution was then concentrated on a rotary evaporator and freeze dried into a powder.

Examples of substances prepared by this method include the following:

1) ethanediyl-1,2-bis(dimethyldecylammonium chloride)
2) ethanediyl-1,2-bis(dimethyldecylammonium iodide)
3) ethanediyl-1,2-bis(dimethyldecylammonium dihydrogenphosphate)
4) ethanediyl-1,2-bis(dimethyldecylammonium thiosulfate)
5) ethanediyl-1,2-bis(dimethyldecylammonium sulfate)
6) ethanediyl-1,2-bis(dimethyldecylammonium oxalate)

Example 3

Preparation of Liposomes

Liposomes may be prepared by combining a cationic cytofectin as provided herein and a neutral lipid, DOPE by the method provided below. Such liposomes include Q203, Q205, Q206, Q208, and Q817 (see Table 1).

Materials:

Chloroform (Merk, p.a.), endotoxin free deionized water, a solution of DOPE in chloroform and a cationic cytofectin.

Method:

Briefly, a cationic cytofectin and a neutral lipid was mixed together for a final concentration of 2 mM in chloroform, which was then evaporated off in a rotary evaporator at 60° C. The mixture was dried for 10 minutes under a reduced pressure of 10 to 15 mbar. Under sterile conditions, endotoxin free deionized water was added to the mixture, which was then heated while stirring at 60° C.

Next, some solutions were sonicated once for 300 seconds at 60° C. (e.g., those whose end products are Q203 and Q205). Other solutions not sonicated but were stirred at 60° C. until the solutions became transparent or slightly opalescent (e.g., those end products are Q206, Q208 and Q817). The total concentration of DOPE+cationic cytofectin for all liposomes was 2 mM. The concentration of DOPE in each liposome can be calculated by multiplying the X(DOPE) value in Table 1 by 2 mM so that, for example, Q203-containing liposomes are 1.7 mM DOPE and 0.3 mM Q203. Table 1 (below) summarizes the cationic cytofectin liposomes used in the methods of this invention. Table 1 gives an overview.

TABLE 1

| Cationic Cytofectin Liposome Reagent | Cationic Cytofectin | X(DOPE) | Method of Preparation |
|---|---|---|---|
| Q203 (18-4-18) | butandiyl-1,4-bis(octadecyl dimethylammonium bromide) | 0.85 | with sonication. |
| Q205 (18-4-18) | butandiyl-1,4-bis(octadecyl dimethylammonium bromide) | 0.82 | with sonication. |
| Q206 (18-4-18) | butandiyl-1,4-bis(octadecyl dimethylammonium bromide) | 0.78 | without sonication. |
| Q208 (18-4-18) | butandiyl-1,4-bis(octadecyl dimethylammonium bromide) | 0.75 | without sonication. |
| Q817 | N,N',N''-trihexadecyl-N,N',N''-pentamethyl-bis-(2-ammonioethyl) ammoniumbromide | 0.80 | without sonication. |

In another example, a liposome consisting of propandiyl-1,3-bis(decyl dimethyl ammonium bromide) (10-3-10) and 1,2 dioleoyl-sn-glycero 3-phosphoethanolamine (DOPE) was made (with X(DOPE)=0.50).

Materials

Chloroform (Merck, p.a.), endotoxin free deionized water, a solution of DOPE in chloroform and 10-3-10.

Method

First a solution was prepared containing 1.17 ml of a 85,21 mg/ml DOPE solution and 57.3 mg 10-3-10 in chloroform. The solvent was eliminated by a rotary evaporator at 60° C. The lipid film was dried for 10 min under a reduced pressure of 10 to 15 mbar. Under sterile conditions 100 ml of endotoxin free deionized water was added to the lipid film containing flask. The flask was heated under stirring to 60° C. until a transparent or slightly opalescent solution was obtained. The final total concentration of DOPE and 10-3-10 of this liposome solution was 2 mM.

When sonicated samples were prepared, an additional ultrasonic treatment of the solution was performed for 300 s with a commercially available sonicator.

Example 4

Transfection Experiments

Liposome-preparation with and without Sonication/cell-specificity of Reagents

Liposomes were prepared at 60° C. by combining 10-3-10 (Propandiyl-1,3-bis(decyl dimethylammonium bromide) and DOPE (as described in Example 3), with and without sonication.

Liposomes were used to transfect HeLaS3 and COS7 cells in vitro with the reporter plasmid pCMVβ (Clontech). Transfection efficiencies, as obtained by optical density (OD) measurements after cell-lysis and β-Gal activity assay, were compared to efficiencies obtained in parallel with a commercially available liposome-preparation (Lipofectamine, Gibco LTI) and given as percentage of Lipofectamine efficiency. For each transfection, 1 μg of pCMVβ (isolated with EndoFree, QIAGEN) was used per well of a 96-well plate. The DNA was diluted to 50 μl with DMEM medium (Gibco LTI) and combined with 1, 2, 3 and 4 μl of the liposome preparations subsequently diluted to 50 μl with DMEM medium. DNA and liposome solutions were mixed and applied to the cells for 6 hours at 37° C., 5% $CO_2$. Afterwards, medium was changed to DMEM containing 10% fetal calf serum. Cells were lysed after 48 h incubation at 37° C., 5% $CO_2$.

Twofold determinations each were performed. The values were averaged and the highest efficiency (optimum) within a row was given as percentage value of the highest efficiency (optimum) obtained with Lipofectamine. The results are shown in Table 2.

TABLE 2

| | | Results % | |
|---|---|---|---|
| X(DOPE) | Preparation | HeLaS3 | COS7 |
| 0.65 | sonic. For 300 s | 83 | 8 |
| 0.50 | sonic. for 300 s | 47 | 6 |
| 0.35 | sonic. for 300 s | 39 | 6 |
| 0.20 | sonic. for 300 s | 39 | 6 |
| 0.65 | w/o sonication | 275 | 26 |
| 0.50 | w/o sonication | 115 | 7 |
| 0.35 | w/o sonication | 61 | 6 |
| 0.20 | w/o sonication | 39 | 6 |

Conclusions:

a) Transfection efficiency for HeLaS3 and COS7 cells is higher if no sonication is used for the preparation of liposomes.
b) The liposomes produced with 10-3-10 (Propandiyl-1,3-bis(decyl dimethylammonium bromide) as cationic component are more cell-type specific than Lipofectamine.

Variations in Hydrophobic Side Chain Length (R) and Transfection Efficiency/specificity Without sonication, liposomes were prepared at 60° C. by combining DOPE with one of the following:

1) 10-2-10 (Ethanediyl-1,2-bis(decyl dimethylammonium bromide)
2) 12-2-12 (Ethanediyl-1,2-bis(dodecyl dimethylammonium bromide)
3) 14-2-14 (Ethanediyl-1,2-bis(tetradecyl dimethylammonium bromide)
4) 16-2-16 (Ethanediyl-1,2-bis(hexadecyl dimethylammonium bromide)

5) 18-2-18 (Ethanediyl-1,2-bis(octadecyl dimethylammonium bromide).

The resulting liposomes were used to transfect Huh7 cells in vitro with the reporter plasmid pCMVβ (Clontech). Transfection efficiencies, as obtained by OD measurements after cell-lysis and β-Gal activity assay, were compared to efficiencies obtained in parallel with a commercially available liposome-preparation (Lipofectamine, Gibco LTI) and given as percentage of Lipofectamine efficiency. For each transfection, 0.5 μg of pCMVβ (isolated with EndoFree, QIAGEN) was used per well of a 96 well plate. The DNA was diluted to 50 μl with DMEM medium (Gibco LTI) and combined with 1, 2, 3 and 4 μl of the liposome preparations subsequently diluted to 50 μl with DMEM medium. DNA and liposome solutions were mixed and applied to the cells for 6 hours at 37° C., 5% $CO_2$. Afterwards, medium was changed to DMEM containing 10% fetal calf serum. Cells were lysed after 48 h incubation at 37° C., 5% $CO_2$. Twofold determinations each were performed. The values were averaged and the highest efficiency (optimum) within a row was given as percentage value of the highest efficiency (optimum) obtained with Lipofectamine. The results are shown in Table 3.

TABLE 3

| Compound | X(DOPE) | Result (%) |
|---|---|---|
| 10-2-10 | 0.50 | 142 |
| 10-2-10 | 0.60 | 127 |
| 10-2-10 | 0.70 | 111 |
| 10-2-10 | 0.80 | 115 |
| 12-2-12 | 0.50 | 70 |
| 12-2-12 | 0.60 | 127 |
| 12-2-12 | 0.70 | 138 |
| 12-2-12 | 0.80 | 89 |
| 14-2-14 | 0.50 | 48 |
| 14-2-14 | 0.60 | 74 |
| 14-2-14 | 0.70 | 98 |
| 14-2-14 | 0.80 | 157 |
| 16-2-16 | 0.50 | 104 |
| 16-2-16 | 0.60 | 124 |
| 16-2-16 | 0.70 | 126 |
| 16-2-16 | 0.80 | 169 |
| 18-2-18 | 0.50 | 82 |
| 18-2-18 | 0.60 | 68 |
| 18-2-18 | 0.70 | 105 |
| 18-2-18 | 0.80 | 115 |

Conclusions:

These results indicate that in transfections with Huh7 cells:
a) increases in side chain lengths lead to a shift in the optimal X(DOPE) value. In the case of 10-2-10, optimal X(DOPE) value is not more than 0.50. In the case of 12-2-12, optimal X(DOPE) value is 0.70. In the case of 14-2-14, 16-2-16 and 18-2-18 the optimal X(DOPE) value is at least 0.80.
b) The optimal length of the hydrophobic side chain in this row is 16. (For HeLaS3 cells, the optimal length of the hydrophobic side chain is 10. For LMH cells, the optimal length of the hydrophobic side chain is 16. For COS7 cells, the optimal length of the hydrophobic side chain is 14—data not shown.)

Variations in Bridge Length (k) and Transfection Efficiency/specificity

Without sonication, liposomes were prepared at 60° C. by combining DOPE with one of the following:
1) 10-2-10 (Ethanediyl-1,2-bis(decyl dimethyl-ammonium bromide)
2) 10-3-10 (Propanediyl-1,3-bis(decyl dimethyl-ammonium bromide)
3) 10-4-10 (Butanediyl-1,4-bis(decyl dimethyl-ammonium bromide)

The resulting liposomes were used to transfect HeLaS3 and Huh7 cells in vitro with the reporter plasmid pCMVβ (Clontech). Transfection efficiency values, obtained by taking OD measurements after cell-lysis and β-Gal activity assay, were compared to efficiencies obtained in parallel with a commercially available liposome-preparation (Lipofectamine, Gibco LTI) and given as percentage of Lipofectamine efficiency. In each transfection, 0.5 μg of pCMVβ (isolated with EndoFree, QIAGEN) was used per well of a 96 well plate. The DNA was diluted to 50 μl with DMEM medium (Gibco LTI) and combined with 1, 2, 3 and 4 μl of the liposome preparations subsequently diluted to 50 μl with DMEM medium. DNA and liposome solutions were mixed and applied to the cells for 6 hours at 37° C., 5% $CO_2$. Afterwards, medium was changed to DMEM containing 10% fetal calf serum. Cells were lysed after 48 h incubation at 37° C., 5% $CO_2$.

Twofold determinations each were performed. The values were averaged and the highest efficiency (optimum) within a row was given as percentage value of the highest efficiency (optimum) obtained with Lipofectamine. The results are shown in Table 4.

TABLE 4

| | | Results (%) | |
|---|---|---|---|
| cytofectin | X(DOPE) | HeLaS3 | Huh7 |
| 10-2-10 | 0.50 | 216 | 142 |
| 10-2-10 | 0.60 | 286 | 127 |
| 10-2-10 | 0.70 | 165 | 111 |
| 10-2-10 | 0.80 | 178 | 115 |
| 10-3-10 | 0.50 | 241 | 80 |
| 10-3-10 | 0.60 | 293 | 83 |
| 10-3-10 | 0.70 | 223 | 54 |
| 10-3-10 | 0.80 | 118 | 39 |
| 10-4-10 | 0.50 | 200 | 76 |
| 10-4-10 | 0.60 | 257 | 62 |
| 10-4-10 | 0.70 | 200 | 54 |
| 10-4-10 | 0.80 | 123 | 34 |

Conclusions:

Structural changes in the cationic cytofectin concerning the bridge length can be used to:
a) make the transfection reagent more efficient in a given cell line (Huh7: decreasing the bridge length leads to increasing efficiency; this is not the case for HeLaS3);
b) make the transfection reagent more specific for a given cell line (by increasing the bridge length, transfection efficiency in HeLaS3 is constant, whereas transfection efficiency in Huh7 drops, thus leading to a more specific transfection reagent for HeLaS3).

Counter Ions Other Than Bromide Used in Preparing Cytofectins: Transfection Efficiency According to this invention, cationic cytofectins may be prepared with counter ions other than bromine as described in Example 2. For example, ethanediyl-1,2-bis(decyl dimethyl ammonium)-chloride, -iodide, -phosphate, -sulfate, -thiosulfate or -oxalate may be prepared.

Without sonication, liposomes were prepared at 60° C. by combining DOPE with one of the following cytofectins:
1) 10-2-10 Ethanediyl-1,2-bis(decyl dimethylammonium) oxalate
2) 10-2-10 Ethanediyl-1,2-bis(decyl dimethylammonium) thiosulfate
3) 10-2-10 Ethanediyl-1,2-bis(decyl dimethylammonium) iodide 4) 10-2-10 Ethanediyl-1,2-bis(decyl dimethylammonium) dihydrogenphosphate Liposomes were used to transfect HeLaS3 cells in vitro with the reporter plasmid pCMVβ (Clontech). Transfection efficiency values, obtained by taking OD measurements after cell-lysis and β-Gal activity assay, were compared with transfection efficiency values from parallel studies with commercially available liposome preparations (Lipofectamine, Gibco LTI) and given as percentage of Lipofectamine efficiency. In each transfection, 0.5 μg of pCMVβ (isolated with EndoFree, QIAGEN) was used per well of a 96 well plate. The DNA was diluted to 50 μl with DMEM medium (Gibco LTI) and combined with 1,2,3 and 4 μl of the liposome preparations subsequently diluted to 50 μl with DMEM. DNA and liposome solutions were mixed and applied to the cells for 6 hours at 37° C., 5% $CO_2$. Afterwards, the medium was changed to DMEM containing 10% fetal calf serum. Cells were incubated for 48 hours at 37° C., 5% $CO_2$ and then lysed.

The results below (Table 5) indicate the optimal transfection efficiency of the reporter plasmid pCMVβ using the above-mentioned liposomes as a percentage of the highest transfection efficiency obtained by Lipofectamine.

TABLE 5

| Counter Ion | X(DOPE) | Results (%) |
|---|---|---|
| sulfate | 0.50 | 879 |
| sulfate | 0.60 | 927 |
| sulfate | 0.70 | 265 |
| sulfate | 0.80 | 1201 |
| oxalate | 0.50 | 275 |
| oxalate | 0.60 | 0 |
| oxalate | 0.70 | 0 |
| oxalate | 0.80 | 0 |
| thiosulfate | 0.50 | 1552 |
| thiosulfate | 0.60 | 1915 |
| thiosulfate | 0.70 | 605 |
| thiosulfate | 0.80 | 844 |
| iodide | 0.50 | 3230* |
| iodide | 0.60 | 3230* |
| iodide | 0.70 | 686 |
| iodide | 0.80 | 457 |
| dihydrogenphosphate | 0.50 | 1966 |
| dihydrogenphosphate | 0.60 | 3230* |
| dihydrogenphosphate | 0.70 | 580 |
| dihydrogenphosphate | 0.80 | 615 |

*this percentage value reflects the upper limit of the β-Gal assay, real values are higher.

In similar studies in HeLaS3 cells, the same vector was transfected with liposomes comprising bromide counter ions and the cytofectin, 10-2-10 Ethandiyl-1,2-bis(decyl dimethylammonium). The results are as follows (Table 6):

TABLE 6

| Counter Ion | X(DOPE) | Results (%) |
|---|---|---|
| bromide | 0.50 | 216 |
| bromide | 0.60 | 286 |
| bromide | 0.70 | 165 |
| bromide | 0.80 | 178 |

Generally, liposomes comprising cationic cytofectins prepared with the above-mentioned counter ions were more effective in delivering DNA than Lipofectamine in the above mentioned transfections. For example, transfections with cytofectins prepared with sulfate, thiosulfate, iodide, and dihydrophosphate counter ions yielded higher transfection efficiency values than transfections with Lipofectamine. The highest transfection efficiencies were achieved with liposomes comprising cationic cytofectins prepared with iodide and dihydrogenphosphate counter ions. Thus, counter ions may be useful in modulating transfection efficiency.

Example 5

Transfection Experiments Using Cationic Cytofectins having Three Nitrogens/ammonium Groups N,N',N''-trialkyl-N,N,N',N'',N''-pentamethyl-bis-(2-ammonioethyl)ammoniumbromide Liposomes comprising compound (3) [synthesis according to Example 1B] and DOPE were prepared at 60° C., using DOPE without sonication.

The resulting liposomes were used to transfect HeLaS3 cells and COS7 cells in vitro with the reporter plasmid pCMVβ (Clontech). Transfection efficiency values, obtained by taking OD measurements after cell-lysis and P-Gal activity assay, were compared with transfection efficiency values from parallel studies with commercially available liposome preparations (Lipofectamine, Gibco LTI) and given as percentage of Lipofectamine efficiency. In each transfection, 0.5 μg of pCMVβ (isolated with EndoFree, QIAGEN) was used per well of a 96 well plate. The DNA was diluted to 50 μl with DMEM medium (Gibco LTI) and combined with 1, 2, 3 and 4 μl of the liposome preparations subsequently diluted to 50 μl with DMEM. DNA and liposome solutions were mixed and applied to the cells for 6 hours at 37° C., 5% $CO_2$. Afterwards, the medium was changed to DMEM containing 10% fetal calf serum. Cells were incubated for 48 hours at 37° C., 5% $CO_2$ and then lysed.

The results below (Table 7) indicate the optimal transfection efficiency of the reporter plasmid pCMVβ using the above-mentioned liposomes as a percentage of the highest transfection efficiency obtained by Lipofectamine. R indicates the number of carbons in the alkyl chain. Concentration of DOPE in each liposome may be calculated by multiply the X(DOPE) value by 2M.

TABLE 7

| | | Results | |
|---|---|---|---|
| R = | X(DOPE) | HeLaS3 (%) | COS7 (%) |
| 10 | 0.50 | 231 | 11 |
| 10 | 0.6 | 222 | 9 |
| 10 | 0.7 | 52 | 16 |
| 10 | 0.8 | 47 | 20 |
| 12 | 0.5 | 0 | 3 |
| 12 | 0.6 | 9 | 5 |
| 12 | 0.7 | 17 | 8 |
| 12 | 0.8 | 63 | 29 |
| 14 | 0.5 | 7 | 8 |
| 14 | 0.6 | 7 | 9 |
| 14 | 0.7 | 9 | 12 |
| 14 | 0.8 | 35 | 58 |
| 16 | 0.5 | 31 | 18 |
| 16 | 0.6 | 39 | 16 |
| 16 | 0.7 | 70 | 44 |
| 16 | 0.8 | 75 | 38 |
| 18 | 0.5 | 65 | 20 |
| 18 | 0.6 | 61 | 34 |
| 18 | 0.7 | 80 | 79 |
| 18 | 0.8 | 61 | 93 |

A) Cationic cytofectins having the chemical formula, N,N',N''-trialkyl-N,N',N''-amethyl-bis-(2-ammonioethyl) ammoniumbromide, can transfect cell lines in vitro.

B) Different alkyl groups attached to the nitrogen alter the specificity for different cell lines. Whereas HeLaS3 cells were best transfected by using chain length of 10, COS 7 cells showed their optimum at a chain length of 18.

What is claimed is:

1. A method for delivering exogenous compounds into cells comprising the steps of:

(a) preparing a formulation comprising a compound according to Formula (I),

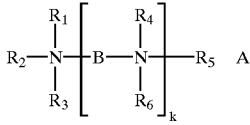

Formula (I)

wherein

A denotes an anion selected from the group of chloride, bromide, iodide, hydrogenphosphate ($HPO_4^{2-}$), dihydrogenphosphate ($H_2PO_4=$), sulphate, thiosulphate, hydroxy and/or oxalate;

k denotes an integer 1, 2, 3, 4 or 5;

B denotes an alkandiyl bridge $(CH_2)_n$; wherein n denotes an integer 1, 2, 3, 4, 5, 6, 7, 8, 9 or 10;

$R_1$, $R_3$ and $R_4$, which may be identical to one another or different, denote hydrogen, straight-chained or branched $C_1$–$C_6$-alkyl, $C_1$–$C_6$-alkenyl, $C_1$–$C_6$-alkynyl;

$R_2$ denotes straight-chained or branched $C_8$–$C_{20}$-alkyl, $C_8$–$C_{20}$-alkenyl, $C_8$–$C_{20}$-alkynyl;

$R_5$ denotes for k=1
   straight-chained or branched $C_8$–$C_{20}$-alkyl, $C_8$–$C_{20}$-alkenyl, $C_8$–$C_{20}$-alkynyl;
denotes for k>1
   hydrogen, straight-chained or branched $C_1$–$C_6$-alkyl, $C_1$–$C_6$-alkenyl, $C_1$–$C_6$-alkynyl;

$R_6$ denotes for k=1
   hydrogen, straight-chained or branched $C_1$–$C_6$-alkyl, $C_1$–$C_6$-alkenyl, $C_1$–$C_6$-alkynyl;
denotes for k>1
   a straight-chained or branched $C_8$–$C_{20}$-alkyl, $C_8$–$C_{20}$-alkenyl, $C_8$–$C_{20}$-alkynyl;

and the repeating unit —B—$NR_4R_6$ may be identical to one another or different; and an exogenous compound desired to be introduced into cells, and (b) contacting the formulation with one or more cells.

2. The method according to claim 1, wherein,

A denotes an anion selected from the group of chloride, bromide, iodide, hydrogenphosphate ($HPO_4^{2-}$), dihydrogenphosphate ($H_2PO_4-$), sulphate, thiosuiphate, hydroxy and/or oxalate;

k denotes an integer 1, 2 or 3;

B denotes an alkandiyl bridge (—$CH_2)_n$—; and n denotes an integer 1, 2, 3, 4, 5 or 6;

$R_1$, $R_3$ and $R_4$, which may be identical to one another or different, denote hydrogen or straight-chained or branched $C_1$–$C_6$-alkyl;

$R_2$ denotes straight-chained or branched $C_8$–$C_{20}$-alkyl, $C_8$–$C_{20}$-alkenyl, $C_8$–$C_{20}$-alkynyl;

$R_5$ denotes for k=1
   a straight-chained or branched $C_8$–$C_{20}$-alkyl, $C_8$–$C_{20}$-alkenyl, $C_8$–$C_{20}$-alkynyl
denotes for k>1
   hydrogen, straight-chained or branched $C_1$–$C_6$-alkyl;

$R_6$ denotes for k=1
   hydrogen, straight-chained or branched $C_1$–$C_6$-alkyl, $C_1$–$C_6$-alkenyl, $C_1$–$C_6$-alkynyl;
denotes for k>1
   a straight-chained or branched $C_8$–$C_{20}$-alkyl, $C_8$–$C_{20}$-alkenyl, $C_8$–$C_{20}$-alkynyl and the repeating unit —B—$NR_4R_6$ is preferably identical to one another.

3. The method according to claim 1, wherein

A denotes an anion selected from the group of bromide, iodide, dihydrogenphosphate ($H_2PO_4$—) and/or thiosulphate;

k denotes an integer 1 or 2;

B denotes for k=1
   an alkandiyl bridge —$(CH_2)_n$ wherein
      n represents an integer 2, 3 or 4;
   denotes for k=2
      an ethylene bridge —$(CH_2$—$CH_2)$—;

$R_1$, $R_3$ and $R_4$, which are identical to one another, denote $CH_3$;

$R_2$ denotes straight-chained $C_{10}$–$C_{20}$-alkyl;

$R_5$ denotes for k=1
   straight-chained $C_{10}$–$C_{20}$-alkyl and is identical to $R_2$;
denotes for k=2
   $CH_3$;

$R_6$ denotes for k=1
   $CH_3$
denotes for k=2
   straight-chained $C_{10}$–$C_{20}$-alkyl and is identical to $R_2$.

4. The method according to claim 1, wherein said compound is part of a liposome further comprising a neutral lipid or lipid like compound.

5. The method according to claim 4, wherein said neutral lipid or lipid like compound is dioleoylphosphatidylethanolamine (DOPE) and/or 1,2-dioleoyloxiphosphatidylethanolamine and/or Cholesterole and/or Dioleyl-phosphatidyicholin (DOPC).

6. The method according to claim 1 or 4, wherein said compound comprises a cell targeting component.

7. The method according to claim 6, wherein said cell targeting compound is a ligand or ligand-like component for a specific cell surface receptor or nuclear receptor.

8. The method according to claim 1 or 4 for in vitro transfection of cell cultures, wherein said exogenous compound is DNA, and wherein the DNA/liposome ratio is 0.01 $\mu$g to 1 $\mu$g DNA/$\mu$g liposome.

9. The method according to claim 8, wherein the DNA/liposome ratio is 0.1 $\mu$g to 1 $\mu$g DNA/$\mu$g liposome.

10. The method according to claim 1 or 4 for in vivo transfection, wherein said exogenous compound is DNA, and wherein the DNA/liposome ratio is in the range of DNA/liposome (w/w) 2:1 to 1:3/1 $\mu$g to 100 mg per kg body weight.

11. A kit for transfection, comprising:
(a) liposome preparation components comprising:
a cationic cytofectin of the general Formula (I):

Formula (I)

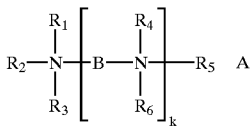

wherein
A denotes an anion selected from the group of chloride, bromide, iodide, hydrogenphosphate ($HPO_4^{2-}$), dihydrogenphosphate ($H_2PO_4=$), sulphate, thiosulphate, hydroxy and/or oxalate;
k denotes an integer 1, 2, 3, 4, or 5;
B denotes an alkandiyl bridge $(CH_2)_n$; wherein
n denotes an integer 1, 2, 3, 4, 5, 6, 7, 8, 9, or 10;
$R_1$, $R_3$ and $R_4$, which may be identical to one another or different, denote hydrogen, straight-chained or branched $C_1$–$C_6$-alkyl, $C_1$–$C_6$-alkenyl, $C_1$–$C_6$-alkynyl;
$R_2$ denotes straight-chained or branched $C_8$–$C_{20}$-alkyl, $C_8$–$C_{20}$-alkenyl, $C_8$–$C_{20}$-alkynyl;
$R_5$ denotes for k=1
straight-chained or branched $C_8$–$C_{20}$-alkyl, $C_8$–$C_{20}$-alkenyl, $C_8$–$C_{20}$-alkynyl;
denotes for k>1
hydrogen, straight-chained or branched $C_1$–$C_6$-alkyl, $C_1$–$C_6$-alkenyl, $C_1$–$C_6$-alkynyl;
$R_6$ denotes for k=1
hydrogen, straight-chained or branched $C_1$–$C_6$-alkyl, $C_1$–$C_6$-alkenyl, $C_1$–$C_6$ alkynyl;
denotes for k>1
a straight-chained or branched $C_8$–$C_{20}$-alkyl, $C_8$–$C_{20}$-alkenyl, $C_8$–$C_{20}$-alkynyl;
and the repeating unit —B—$NR_4R_6$ may be identical to one another or different;
and an exogenous compound desired to be introduced into cells;
(b) buffers useful for transfection.

12. The method according to claim 1 or 4 for the delivery of a nucleic acid, or derivative thereof, into a target cell, wherein the exogenous compound is a nucleic acid, or derivative thereof.

13. The method according to claim 12, characterized in that the nucleic acid is a single stranded or double stranded DNA, a single stranded or double stranded RNA, a DNA/RNA—hybrid, or derivatives thereof.

14. The method according to claim 13, characterized in that the DNA is selected from the group of plasmids, vectors, cDNA, cpG-motifs, and oligonucleotides, and that the RNA is selected from the group of mRNA, oligonucleotides, antisense RNA oligomers, or ribozymes.

15. The method as define in claim 1, wherein the exogenous compound is a pharmaceutical compound.

16. The A method as defined in claim 1, wherein the exogenous compound is a therapeutic vaccine.

17. The method according to claim 1, wherein the $C_1$–$C_6$-alkyl group is substituted with one or more halogens.

18. The method according to claim 17, wherein the halogen is fluorine.

19. The method according to claim 1, wherein the $C_1$–$C_6$-alkyl group is selected from the group consisting of methyl, ethyl, propyl, isopropyl, butyl, 1-methylpropyl, 2-methylpropyl, 1,1-dimethylethyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, and 1-ethyl-2-methyl-propyl.

20. The method according to claim 19, wherein the alkyl group is methyl, ethyl, n-propyl, or isopropyl.

21. The method according to claim 1, wherein the alkandiyl group is selected from the group consisting of methyl, ethyl, propyl, isopropyl, butyl, 1-methylpropyl, 2-methylpropyl, 1,1-dimethylethyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, and 1-ethyl-2-methyl-propyl.

22. The method according to claims, wherein the alkandiyl group is methyl, ethyl, n-propyl, or isopropyl.

23. The method according to claim 1, wherein $C_8$–$C_{20}$-alkyl is selected from the group consisting of octyl, decyl, undecyl, dodecyl, tridecyl, tetradecyl, pentadecyl, hexadecyl, heptadecyl, dodecadecyl, nonadecyl, and eicosyl.

24. The method according to claim 1, wherein the alkenyl group is selected from the group consisting of 2-propenyl, 2-butenyl, 3-butenyl, 1-methyl-2-propenyl, 2-methyl-2-propenyl, 2-pentenyl,, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-1-butenyl, 2-ethyl-2-butenyl, 2-ethyl-3-butenyl, 1,1,2,-trimethyl-2-propenyl, 1-ethyl-1-methyl-2-propenyl, and 1-ethyl-2-methyl-2-propenyl.

25. The method according to claim 24, wherein the alkyl group is 2-propenyl.

26. The method according to claim 1, wherein the alkynyl group is selected from the group consisting of 2-propynyl, 2-butynyl, 3-butynyl, 2-pentynyl, 3-pentynyl, 4-pentynyl, 3-methyl-2-butynyl, 2-hexynyl, 3-hexynyl, 4-hexynyl, 5-hexynyl, 3-methyl-2-pentynyl, 4-methyl-2-pentynyl, 2-methyl-3-pentynyl, 4-methyl-3-pentynyl, 1-methyl-4-pentynyl, 1,1-dimethyl-2-butynyl, 1,1-dimethyl-2-butynyl, 1,1-dimethyl-3-butynyl, 1 ,2-dimethyl-3-butynyl, 1 , 3-dimethyl-2-butynyl, 2,2-dimethyl-3-butynyl, 1-ethyl-2-butynyl, 1-ethyl-3-butynyl, 2-ethyl-3-butynyl, and 1-ethyl-1-methyl-2-propynyl.

27. The method according to claim 26, wherein the alkynyl group is 2-propynyl.

28. The method according to claim 1 wherein said compound is selected from the group consisting of:
N,N',N"-trioctyl-N,N,N',N",N"-pentamethyl-bis-(2-ammonioethyl)-ammonium bromide;

N,N',N"-tridecyl-N,N,N',N",N"-pentamethyl-bis-(2-ammonioethyl)-ammonium bromide;

N,N',N"-tridodecyl-N,N,N',N",N"-pentamethyl-bis-(2-ammonioethyl)-ammonium bromide;

N,N',N"-tritetradecyl-N,N,N',N",N"-pentamethyl-bis-(2-ammonioethyl)-ammonium bromide;

N,N',N"-trihexadecyl-N,N,N',N",N"-pentamethyl-bis-(2-ammonioethyl)-ammonium bromide;

N,N',N"-trioctadecyl-N,N,N',N",N"-pentamethyl-bis-(2-ammonioethyl)-ammonium bromide;

ethanediyl-1,2-bis(dimethyldecyl ammonium chloride); ethanediyl-1,2-bis(dimethyldecyl ammonium iodide); ethanediyl-1,2-bis(dimethyldecyl ammonium dihydrogenphosphate); ethanediyl-1,2-bis (dimethyldecyl ammonium thiosulfate); ethanediyl-1,2-bis(dimethyldecyl animonium sulfate); ethanediyl-1,2-bis(dimethyldecyl ammonium oxalate); ethanediyl-1,2-bis(decyl dimethyl ammonium bromide); ethanediyl-1,2-bis(dodecyl dimethyl ammonium bromide); ethanediyl-1,2-bis(tetradecyl dimethyl ammonium bromide); ethanediyl-1,2-bis(hexadecyl dimethyl ammonium bromide); ethanediyl-1,2-bis(octadecyl dimethyl ammonium bromide); propanediyl-1,3-bis (decyl dimethyl ammonium bromide); butanediyl-1,4-bis(decyl dimethyl ammonium bromide); and butanediyl-1,4-bis(octadecyl dimethylanimonium bromide).

29. A liposome for delivering an exogenous compound to cells comprising a cytofectin compound according to claim 1 and a neutral lipid or lipid-like molecule.

30. The liposome according to claim 29, wherein the neutral lipid or lipid-like molecule is selected from the group consisting of dioleoylphosphatidylethanolamine (DOPE), 1,2 dioleoyloxiphosphatidylethanolaniine, cholesterol, and dioleoylphosphatidylcholine (DOPC).

31. The liposome according to claim 30, wherein said neutral lipid is DOPE.

32. The liposome according to claim 29, further comprising a helper lipid molecule for preparing liposomes.

33. The liposome according to claim 29, wherein the helper lipid molecule has a hydrolytically stable linkage in place of an ester linkage.

34. The liposome according to claim 29, further comprising a co-lipid molecule used to form a stable liposome.

35. The liposome according to claim 34, wherein the co-lipid molecule is selected from the group consisting of lecithin, phosphatidylcholine, dioleylphosphatidylcholine (DOPC), phosphatidylethanolamine (PE), phosphatidylserine, phosphatidylglycerine, phosphatidylinositole, sphingomyeline, cephaline, cardiolipin, phosphatidic acid, cerebroside, diacetylphosphate, lysophosphatidylethanolamine, dipalmitoylphosphatidylcholine, dioleoylphosphatidylglycerol, dipalmitoylphosphatidyl-glycerol, palmitoyloleoylphosphatidylcholine, palmitoyloleoylphosphatidylethannolamine, diheptadecanoylphosphatidylethanolamine, dilauroylphosphatidylethanolamine, dimyristoylphosphatidylethanolamine, distearoylphosphatidylethanolamine, beta-linoleoylgammapalrnitoyl-phosphatidylethannolamine, and beta-oleoyl-ganima-palmitoylphosphatidylethanolamine.

36. The liposome according to claim 29 further comprising a cell targeting component.

37. The liposome according to claim 34, wherein the cell targeting component is a ligand or ligand-like component for a specific cell surface receptor or nuclear receptor.

38. The liposome according to claim 34, wherein in the cell targeting component is a ligand selected from the group consisting of hormones, carbohydrate ligands, growth factor, neurotransmitters, fragments thereof, and modified forms thereof.

39. The liposome according to claim 34, wherein the cell targeting component is selected from the group consisting of antibodies, lectins, peptides, proteins, carbohydrates, and glycoproteins.

40. The liposome according to claims 38 or 39, wherein the cell targeting component is a neutral co-lipid or negatively charged co-lipid coating the surface of the liposome.

41. The liposome according to claim 29, wherein the exogenous compound is selected from the group consisting of nucleic acids, peptides, peptide derivatives, proteins, protein derivatives, steroids, hormones, carbohydrates, and pharmaceutical compounds.

42. The liposome according to claim 41, wherein the peptide, peptide derivative, protein, or protein derivative are antigeriic.

43. The liposome according to claim 41, wherein the peptide or protein derivatives are selected from the group consisting of cyclic peptides, peptidomimetics, peptides or proteins containing non-natural amino acids, and peptides or proteins containing non-natural bonds between amino acids.

44. The liposome according to claim 41, wherein the nucleic acid is selected from the group consisting of natural nucleic acids, synthetic nucleic acids, single-stranded nucleic acids, double-stranded nucleic acids, genomic DNA, cDNA, plasmids, DNA vectors, antisense nucleic acid, antisense RNA oligomers, ribozymes, DNA oligonucleotides, nucleosides, RNA, DNA/RNA hybrids, nucleic acids containing phosphorothioates, and nucleic acids containing phosphoramidates.

45. The liposome according to claim 44, wherein the plasmid comprises an unmethylated CpG dinucleotide.

46. The liposome according to claim 44, wherein the DNA oligonucleotide is an oligonucleotide that is complementary to a coding region of a gene, a 3' untranslated region of a gene, a transcription control sequence of a gene, or that comprises an unmethylated CpG dinucleotide.

47. The liposome according to claim 41, wherein the DNA/liposome (w/w) ratio isin the range of 2:1 to 1:5.

48. The liposome according to claim 47, wherein the DNA/liposome (w/w) ratio is 1:3.

* * * * *